United States Patent
Tung et al.

(10) Patent No.: US 10,152,998 B2
(45) Date of Patent: Dec. 11, 2018

(54) FEATURES MAPS OF ARTICLES WITH POLARIZED LIGHT

(71) Applicant: SEAGATE TECHNOLOGY LLC, Cupertino, CA (US)

(72) Inventors: David M. Tung, Livermore, CA (US); Joachim Walter Ahner, Livermore, CA (US)

(73) Assignee: Seagate Technology LLC, Cupertino, CA (US)

( * ) Notice: Subject to any disclaimer, the term of this patent is extended or adjusted under 35 U.S.C. 154(b) by 441 days.

(21) Appl. No.: 14/280,343

(22) Filed: May 16, 2014

(65) Prior Publication Data

US 2015/0285743 A1    Oct. 8, 2015

Related U.S. Application Data

(60) Provisional application No. 61/976,496, filed on Apr. 7, 2014.

(51) Int. Cl.
*G01N 21/88* (2006.01)
*G01N 21/55* (2014.01)
(Continued)

(52) U.S. Cl.
CPC ......... *G11B 20/1816* (2013.01); *G01N 21/21* (2013.01); *G01N 21/55* (2013.01);
(Continued)

(58) Field of Classification Search
CPC .... G01N 21/21; G01N 21/211; G01N 21/213; G01N 21/8806; G01N 21/8851;
(Continued)

(56) References Cited

U.S. PATENT DOCUMENTS

| 5,090,811 A * | 2/1992 | Donaldson | G01B 11/255 356/3.03 |
| 5,212,535 A * | 5/1993 | Miyazaki | G01P 3/36 180/169 |

(Continued)

FOREIGN PATENT DOCUMENTS

| DE | 4304815 A1 * | 8/1994 | ............ G01B 11/25 |
| DE | 10049382 A1 * | 4/2002 | ............ G01B 11/25 |

(Continued)

OTHER PUBLICATIONS

International Search Report and Written Opinion dated Jun. 26, 2015 in International Application No. PCT/US2015/020632. 15 pages.

(Continued)

*Primary Examiner* — Sang H Nguyen

(57) ABSTRACT

Provided herein is an apparatus including an imaging lens assembly configured to collect reflected light from a surface of an article; an image sensor configured to receive reflected light from the imaging lens assembly, wherein the imaging lens assembly and the image sensor are each arranged at different angles for focusing on substantially an entire surface of an article; and a processing means configured to process signals from the image sensor corresponding to polarized reflected light and subsequently generate one or more features maps.

15 Claims, 9 Drawing Sheets

Figure 1A:
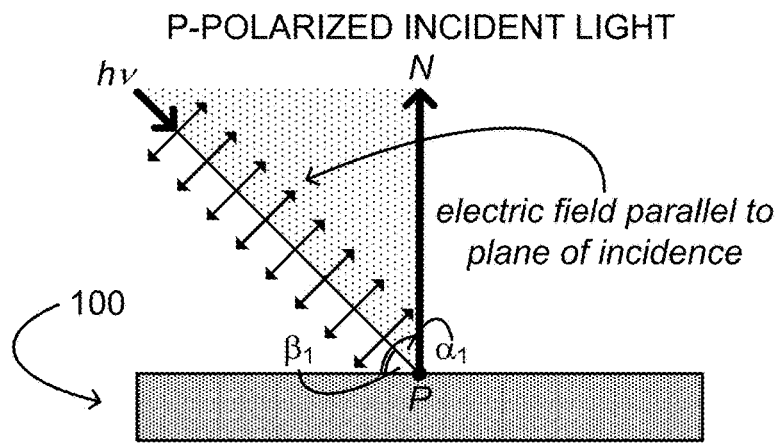

(51) Int. Cl.
*G01N 21/21* (2006.01)
*G11B 20/18* (2006.01)
*G01N 21/95* (2006.01)
*G01B 9/02* (2006.01)

(52) U.S. Cl.
CPC ......... *G01N 21/8806* (2013.01); *G01N 21/95* (2013.01); *G01B 9/02* (2013.01); *G01B 2290/70* (2013.01); *G01N 21/9501* (2013.01); *G01N 21/9506* (2013.01); *G01N 2021/8848* (2013.01); *G01N 2201/06113* (2013.01)

(58) Field of Classification Search
CPC ........... G01N 21/55; G01N 2012/8848; G01B 11/25; G01B 11/0652; G01B 11/0641; G01B 20/1816; G01B 9/02; G01B 2290/70
USPC ....... 356/364–369, 445, 237.1, 237.2, 237.4, 356/237.5; 250/231.11, 201.6, 548.1
See application file for complete search history.

(56) References Cited

U.S. PATENT DOCUMENTS

| | | | |
|---|---|---|---|
| 5,517,312 A | 5/1996 | Finarov | |
| 5,999,249 A * | 12/1999 | Ito | G01C 3/085 250/201.6 |
| 6,665,078 B1 | 12/2003 | Meeks et al. | |
| 6,809,809 B2 * | 10/2004 | Kinney | G01N 21/9501 356/237.1 |
| 6,897,955 B2 | 5/2005 | Welch et al. | |
| 7,329,859 B2 * | 2/2008 | Mizutani | G01D 5/34715 250/231.13 |
| 7,656,519 B2 | 2/2010 | Meeks et al. | |
| 7,724,362 B1 | 5/2010 | Rosengaus | |
| 2002/0054290 A1 | 5/2002 | Vurens et al. | |
| 2004/0119943 A1 * | 6/2004 | Rathjen | A61B 3/1005 351/211 |
| 2005/0094136 A1 | 5/2005 | Xu et al. | |
| 2006/0114470 A1 * | 6/2006 | Takashima | G01B 11/0625 356/453 |
| 2007/0052966 A1 * | 3/2007 | Leidecker | G01J 3/02 356/445 |
| 2007/0121098 A1 * | 5/2007 | Maase | G06K 9/00046 356/71 |
| 2009/0073427 A1 * | 3/2009 | Hackney | G01B 11/2513 356/237.1 |
| 2010/0014088 A1 * | 1/2010 | Wiki | G01N 21/253 356/445 |
| 2012/0050739 A1 | 3/2012 | Hayano | |
| 2012/0120403 A1 | 5/2012 | Funamoto | |
| 2012/0154807 A1 * | 6/2012 | Usami | G01B 11/026 356/369 |

FOREIGN PATENT DOCUMENTS

| | | | |
|---|---|---|---|
| EP | 2538172 A1 * | 12/2012 | .......... G01B 11/026 |
| JP | 2013029438 | 2/2013 | |
| WO | WO 2012042944 A1 * | 4/2012 | .......... G01B 11/026 |

OTHER PUBLICATIONS

PCT International Preliminary Report on Patentability (Chapter I) dated Oct. 20, 2016 in International Application No. PCT/US2015/020632. 16 pages.

* cited by examiner

FEATURES MAPS OF ARTICLES WITH POLARIZED LIGHT

CROSS REFERENCE

This application claims the benefit of U.S. Provisional Patent Application No. 61/976,496, filed Apr. 7, 2014.

BACKGROUND

An article may be inspected for features such as defects that might degrade the performance of the article or a system including the article. For example, a hard disk for a hard disk drive may be fabricated and inspected for defects that might degrade the performance of the hard disk or the hard disk drive. Accordingly, apparatuses and methods may be used to inspect articles for features.

SUMMARY

Provided herein is an apparatus including an imaging lens assembly configured to collect reflected light from a surface of an article; an image sensor configured to receive reflected light from the imaging lens assembly, wherein the imaging lens assembly and the image sensor are each arranged at different angles for focusing on substantially an entire surface of an article; and a processing means configured to process signals from the image sensor corresponding to polarized reflected light and subsequently generate one or more features maps.

These and various other features and advantages will be apparent from a reading of the following detailed description.

DRAWINGS

FIG. 1A provides a schematic illustrating p-polarized incident light upon a surface of an article according to one or more aspects.

Figure 1B:
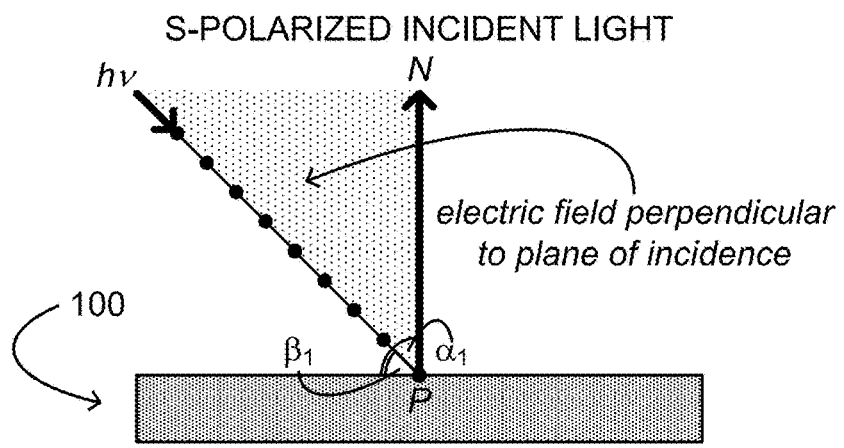

FIG. 1B provides a schematic illustrating s-polarized incident light upon a surface of an article according to one or more aspects.

Figure 1C:
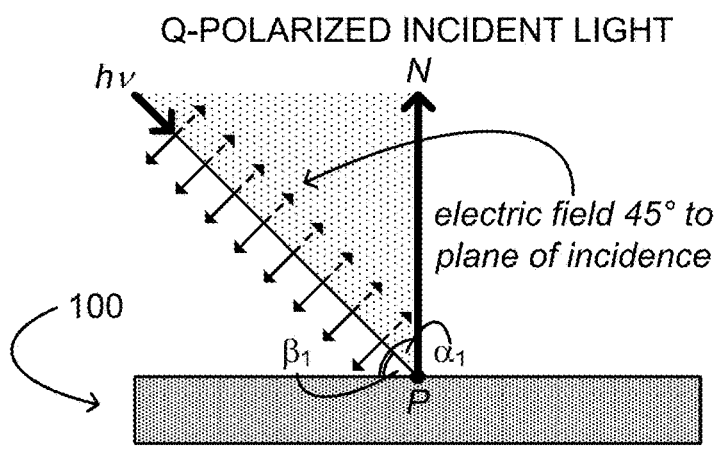

FIG. 1C provides a schematic illustrating q-polarized incident light upon a surface of an article according to one or more aspects.

Figure 1D:
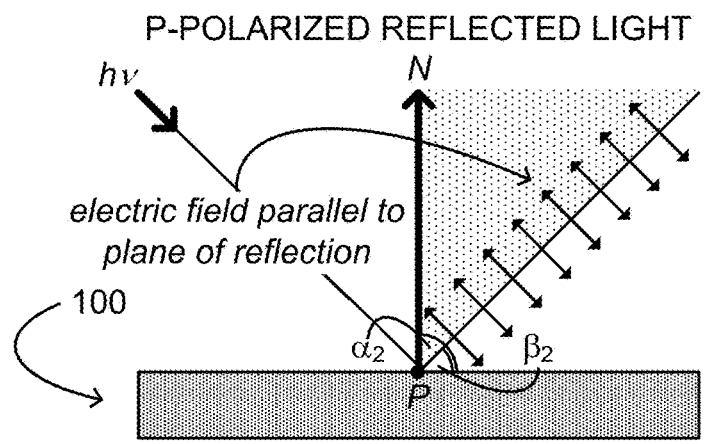

FIG. 1D provides a schematic illustrating p-polarized reflected light from a surface of an article according to one or more aspects.

Figure 1E:
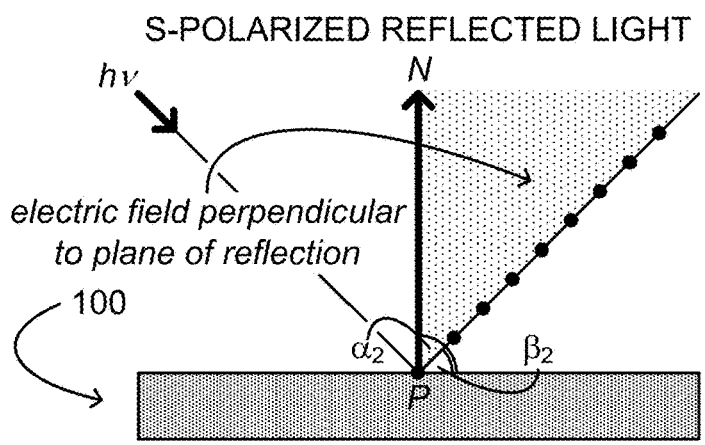

FIG. 1E provides a schematic illustrating s-polarized reflected light from a surface of an article according to one or more aspects.

Figure 1F:
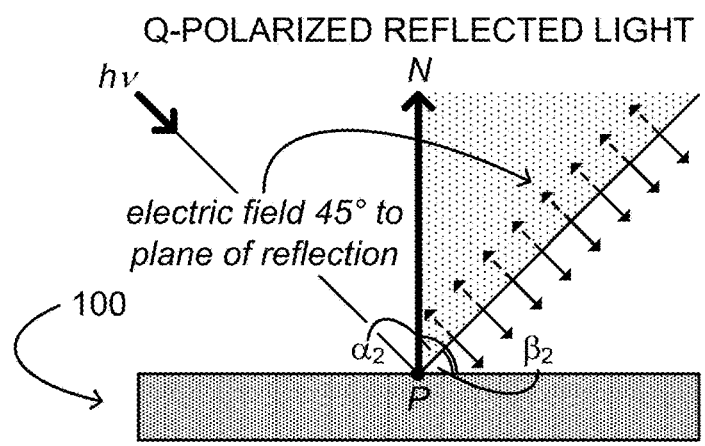

FIG. 1F provides a schematic illustrating q-polarized reflected light from a surface of an article according to one or more aspects.

Figure 2A:
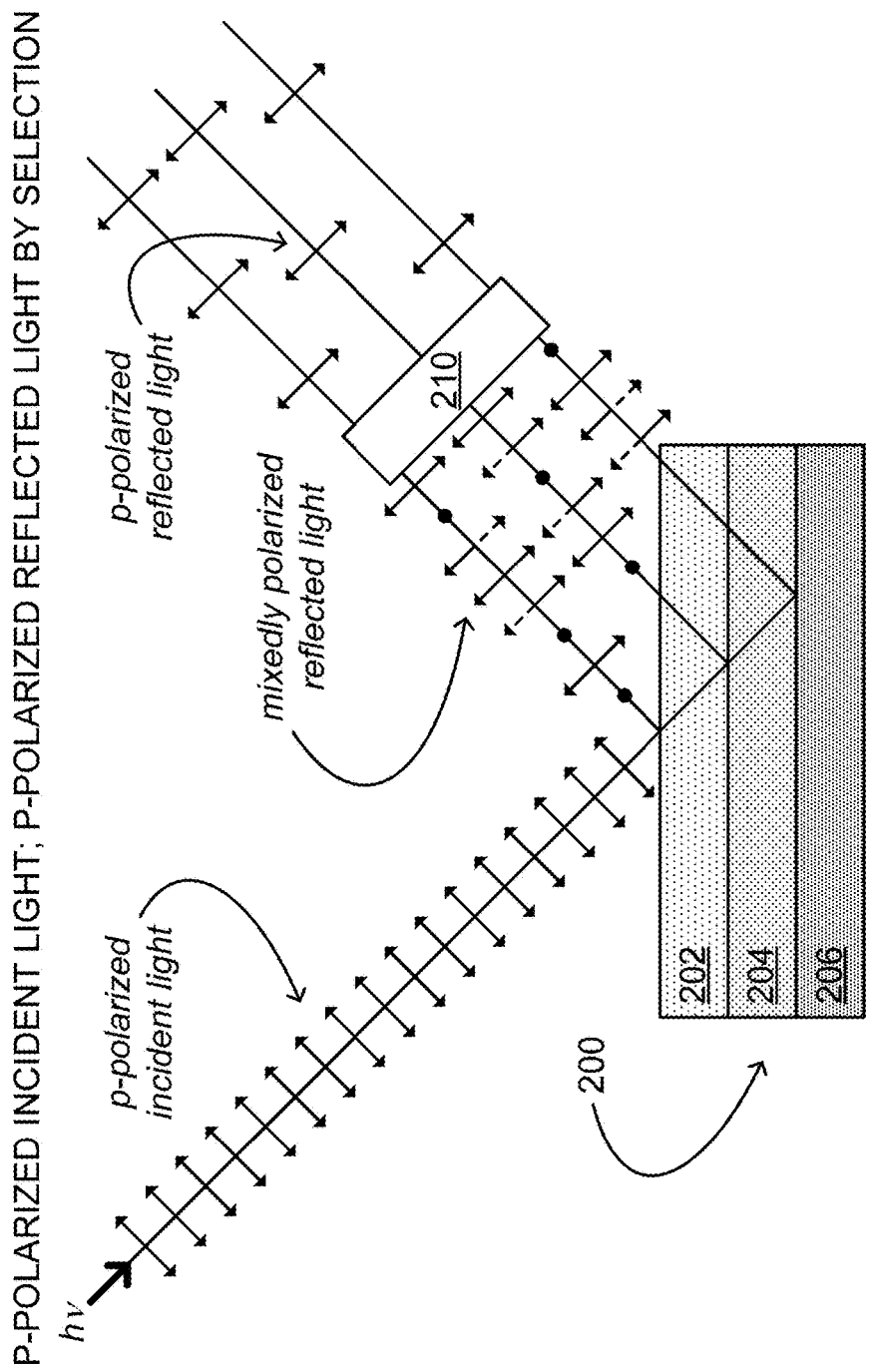

FIG. 2A provides a schematic illustrating p-polarized incident light upon a surface of an article and p-polarized reflected light selected from mixedly polarized reflected light from the surface of the article according to one or more aspects.

Figure 2B:
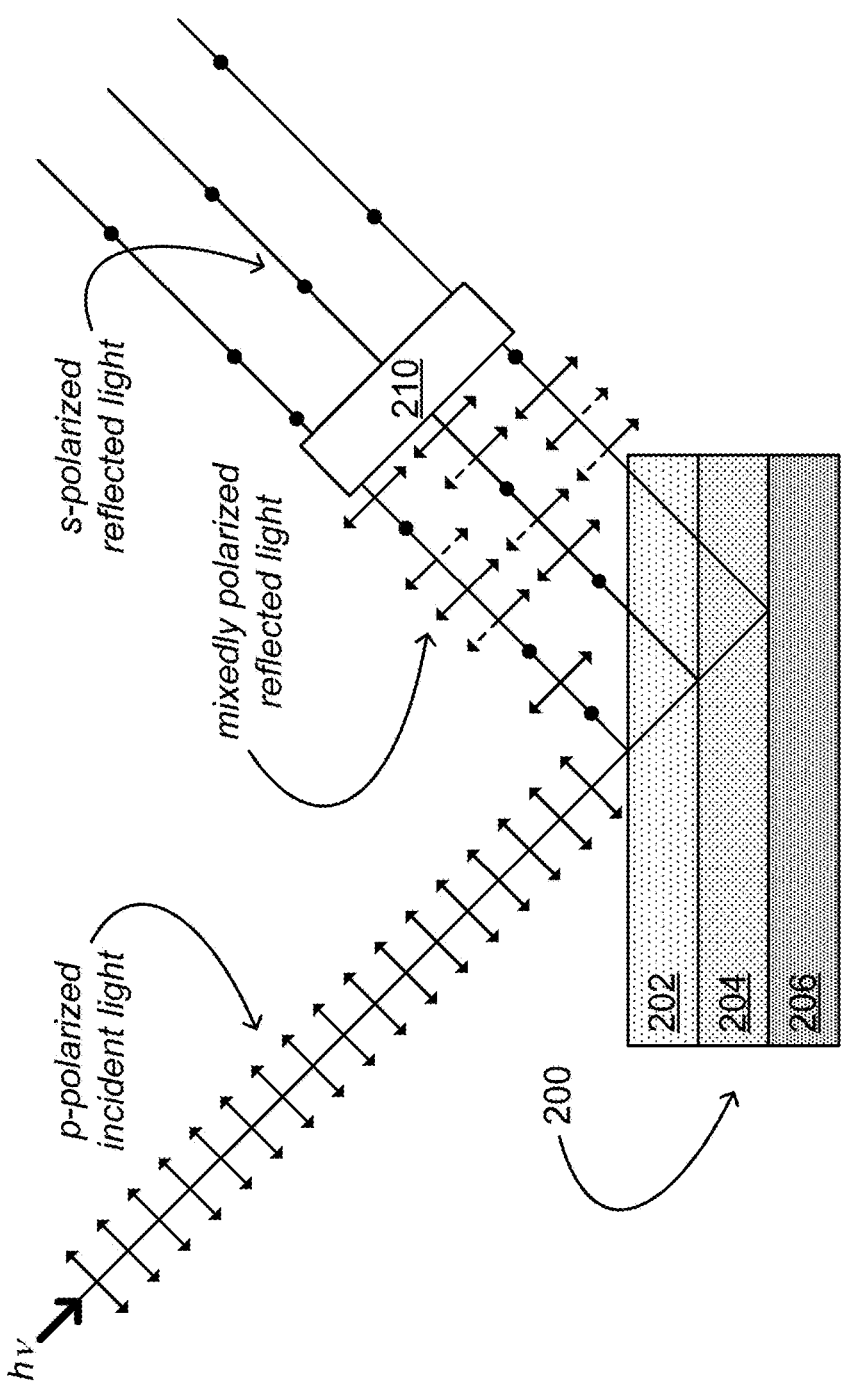

FIG. 2B provides a schematic illustrating p-polarized incident light upon a surface of an article and s-polarized reflected light selected from mixedly polarized reflected light from the surface of the article according to one or more aspects.

Figure 2C:
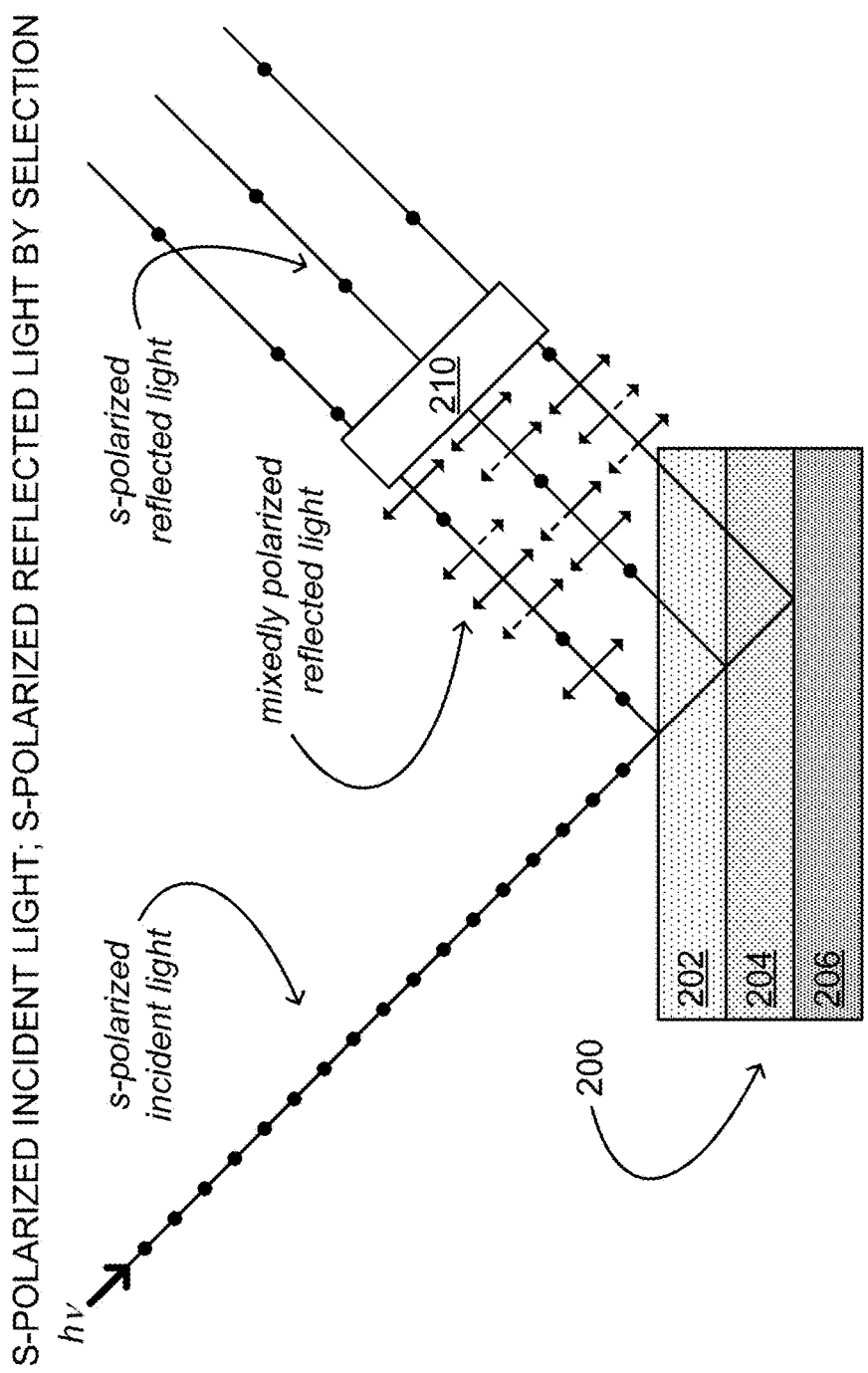

FIG. 2C provides a schematic illustrating s-polarized incident light upon a surface of an article and s-polarized reflected light selected from mixedly polarized reflected light from the surface of the article according to one or more aspects.

Figure 2D:
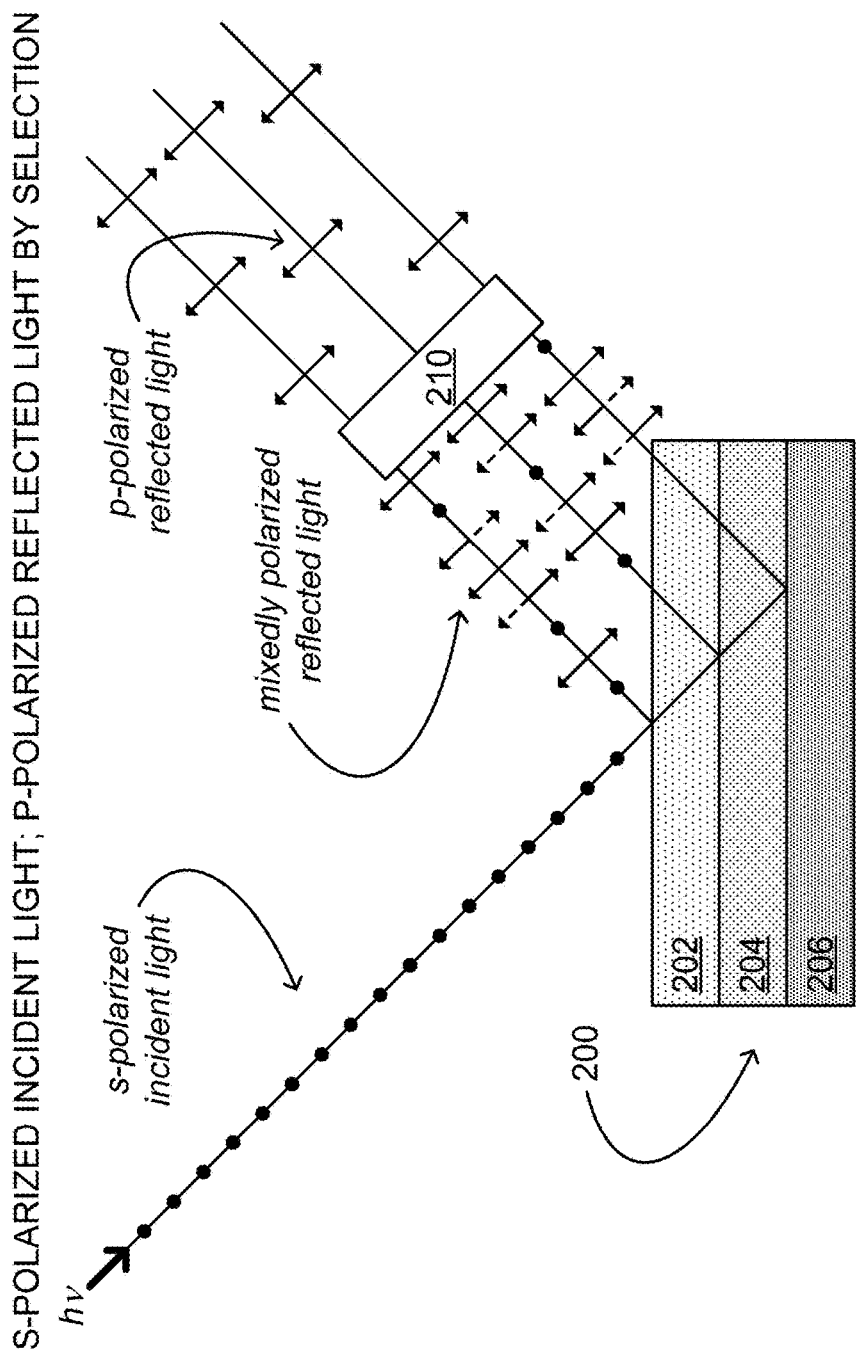

FIG. 2D provides a schematic illustrating s-polarized incident light upon a surface of an article and p-polarized reflected light selected from mixedly polarized reflected light from the surface of the article according to one or more aspects.

Figure 3A:
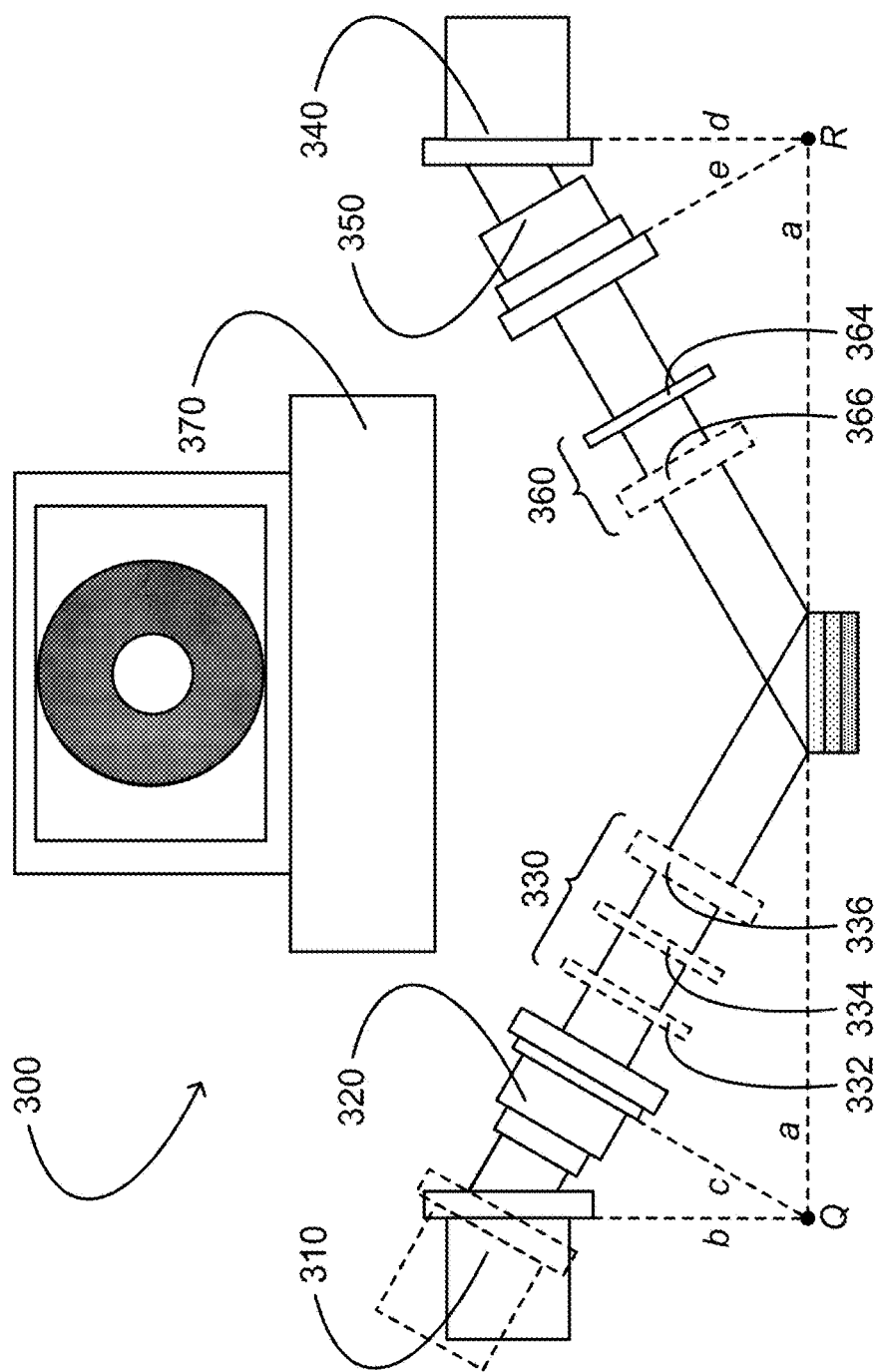

FIG. 3A provides a schematic illustrating detection of features of articles according to one or more aspects.

Figure 3B:
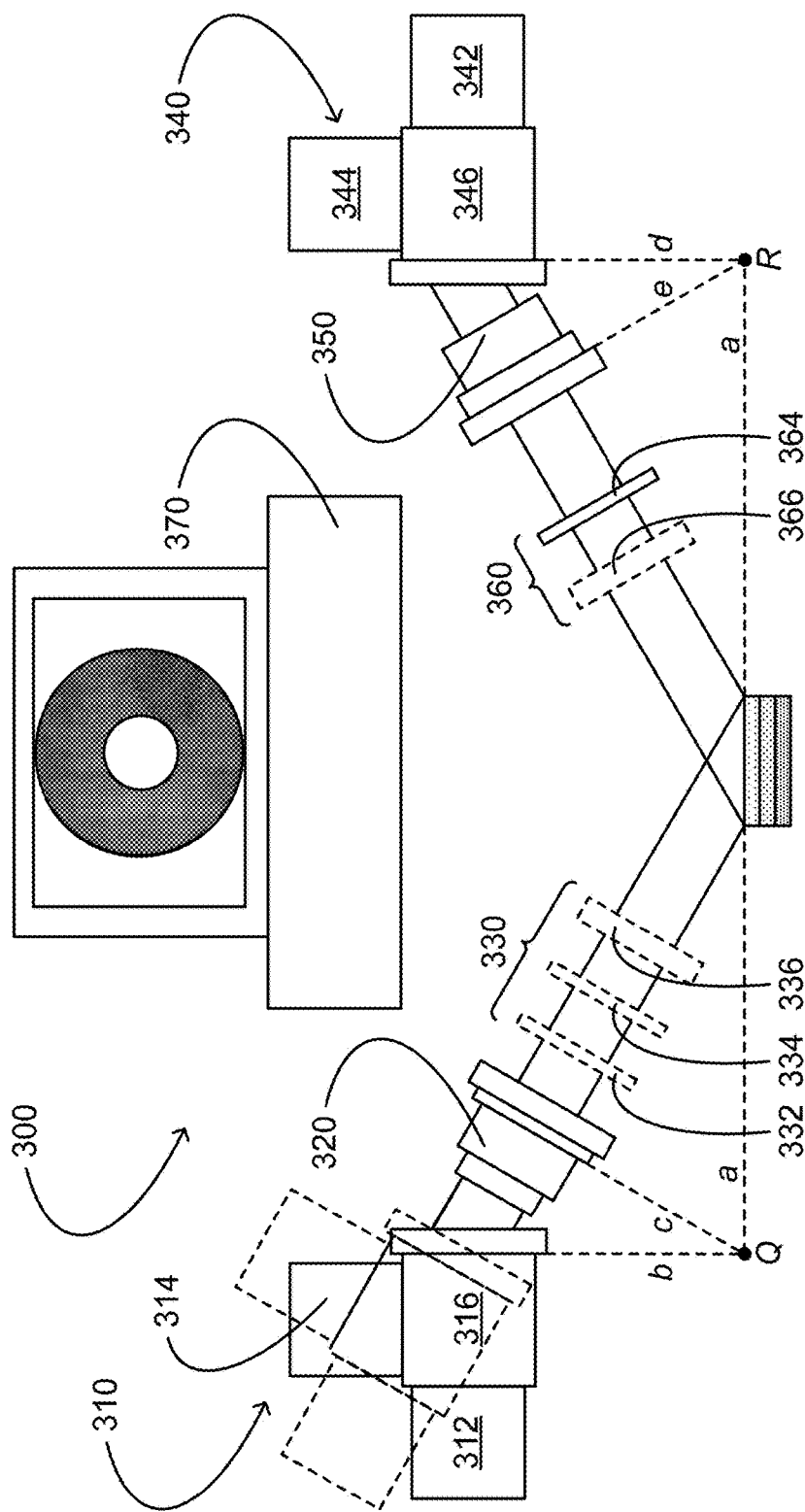

FIG. 3B provides a schematic illustrating detection of features of articles according to one or more aspects.

Figure 4:
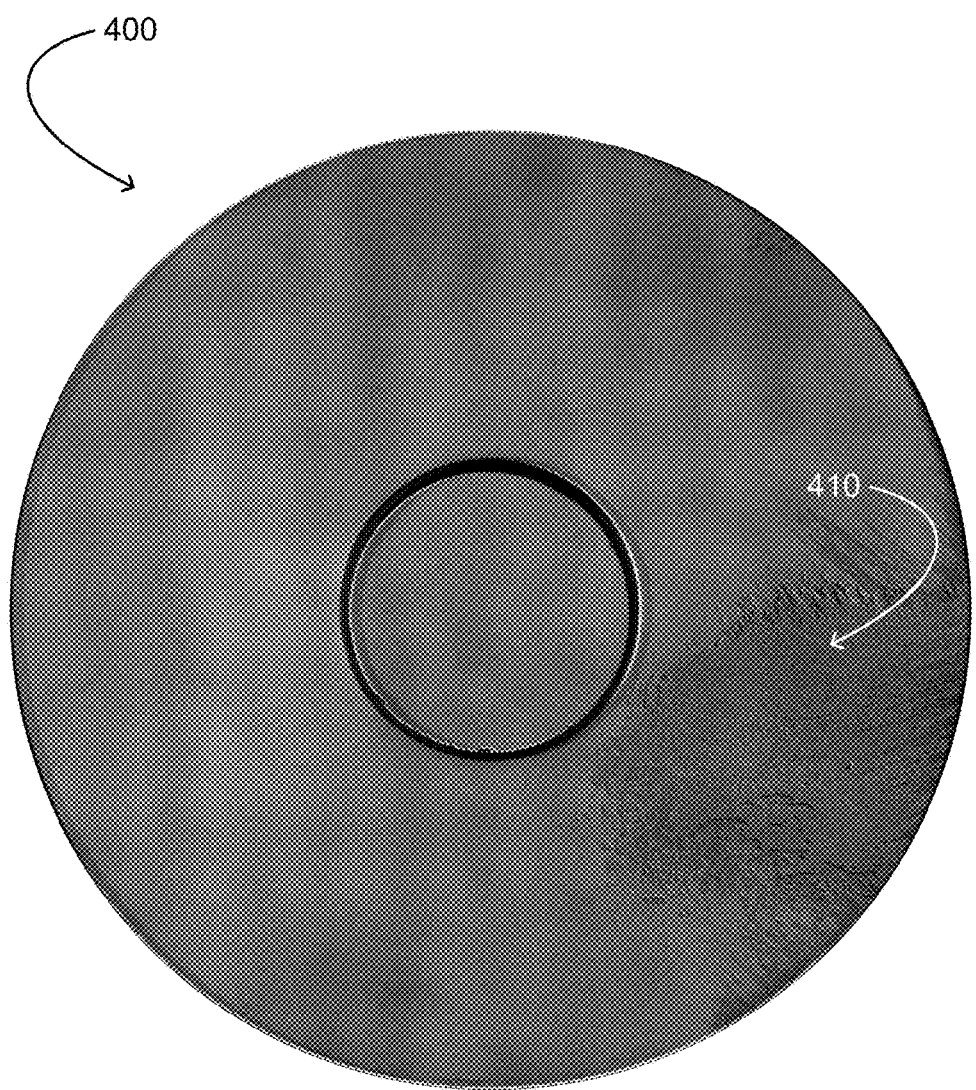

FIG. 4 provides an image of a surface of an article with one or more features including defects according to one or more aspects.

DESCRIPTION

Before some particular embodiments are described and/or illustrated in greater detail, it should be understood by persons having ordinary skill in the art that the particular embodiments described and/or illustrated herein do not limit the concepts provided herein, as features in such particular embodiments may vary. It should likewise be understood that a particular embodiment described and/or illustrated herein has features that may be readily separated from the particular embodiment and optionally combined with or substituted for features in any of several other embodiments described and/or illustrated herein.

It should also be understood by persons having ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," and "down," or other similar terms such as "upper," "lower," "aft," "fore," "vertical," "horizontal," "proximal," and "distal," or the like, are used for convenience and are not intended to imply, for example, any particular fixed location, orientation, or direction. Instead, such labels are used to reflect, for example, relative location, orientation, or direction. It should also be understood that the singular forms of "a," "an," and "the" include plural references unless the context clearly dictates otherwise.

Unless defined otherwise, all technical and scientific terms used herein have the same meaning as commonly understood by persons having ordinary skill in the art.

An article may be inspected for features including defects (e.g., surface and/or subsurface defects) that might degrade the performance of the article or a system including the article. The article may include any article of manufacture or a workpiece thereof in any stage of manufacture having one or more surfaces operable to specularly reflect light. For example, the article may include, but is not limited to, a semiconductor wafer, a magnetic recording medium (e.g., a hard disk for a hard disk drive), or a workpiece thereof in any stage of manufacture.

A hard disk or a workpiece thereof may be inspected for features including defects (e.g., surface and/or subsurface defects) that might degrade the performance of the hard disk or the hard disk drive. For example, hard disks or workpieces thereof may be inspected for stains. For example, hard disks or workpieces thereof having a lubricant layer may be inspected for lubricant layer inhomogeneity including lubricant layer smears, ripples, bumps, and/or depletion. For example, hard disks or workpieces thereof having a carbon overcoat layer may be inspected for carbon overcoat inhomogeneity including carbon overcoat layer voids and/or shadows (e.g., shadows from sputtering clamps).

It is important to inspect articles for features including performance-degrading defects to correct manufacturing trends and to increase product quality. Provided herein are apparatuses and methods for inspecting articles for features including detecting, mapping, and/or distinguishing features of articles, which features include, but are not limited to, defects.

Apparatuses and methods for inspecting articles for features employ various forms of polarized light for detecting, mapping, and/or distinguishing features of articles.

FIGS. 1A-1C provide schematics illustrating some of the various forms of polarized incident light for incident light upon a surface of an article. As shown in each of FIGS. 1A-1C, a plane of incidence may be formed between incident light hv or a ray thereof and a surface normal N to a surface of an article 100 at a point P at which the incident light or ray is incident.

FIG. 1A provides a schematic illustrating p-polarized incident light upon a surface of an article. When incident light is linearly polarized such that the electric field of the incident light is parallel to the plane of incidence, the incident light may be described as p-polarized incident light.

FIG. 1B provides a schematic illustrating s-polarized incident light upon a surface of an article. When incident light is linearly polarized such that the electric field of the incident light is perpendicular to the plane of incidence, the incident light may be described as s-polarized incident light.

FIG. 1C provides a schematic illustrating q-polarized incident light upon a surface of an article. When incident light is linearly polarized such that the electric field of the incident light is 45° to the plane of incidence, the incident light may be described as q-polarized incident light. It should be understood that one of two forms of q-polarized incident light is shown.

As further shown in FIGS. 1A-1C, an angle of incidence $\alpha_1$ may be formed between the incident light or ray and the surface normal. A glancing angle $\beta_1$ may be formed between the incident light or ray and the surface of the article. The glancing angle may also be described as an altitudinal angle between the incident light or ray and the surface of the article. The angle of incidence and the glancing angle are complementary angles.

FIGS. 1D-1F provide schematics illustrating some of the various forms of polarized reflected light for reflected light from a surface of an article. As shown in each of FIGS. 1D-1F, a plane of reflection may be formed between reflected light or a ray thereof and a surface normal N to a surface of an article 100 at a point P at which the reflected light or ray is reflected.

FIG. 1D provides a schematic illustrating p-polarized reflected light from a surface of an article. When the reflected light is linearly polarized such that the electric field of the reflected light is parallel to the plane of reflection, the reflected light may be described as p-polarized reflected light.

FIG. 1E provides a schematic illustrating s-polarized reflected light from a surface of an article. When the reflected light is linearly polarized such that the electric field of the reflected light is perpendicular to the plane of reflection, the reflected light may be described as s-polarized reflected light.

FIG. 1F provides a schematic illustrating q-polarized reflected light from a surface of an article. When the reflected light is linearly polarized such that the electric field of the reflected light is 45° to the plane of reflection, the reflected light may be described as q-polarized reflected light. It should be understood that one of two forms of q-polarized reflected light is shown.

As further shown in FIGS. 1D-1F, an angle of reflection $\alpha_2$ may be formed between the reflected light or ray and the surface normal. An angle $\beta_2$ may be formed between the reflected light or ray and the surface of the article. The angle of reflection and the angle $\beta_2$ are complementary angles. The angle of reflection and the angle of incidence are equal or congruent angles. The angle $\beta_2$ and the glancing angle are equal or congruent angles.

FIGS. 2A-2D provide schematics illustrating some combinations of polarized incident light and polarized reflected light for inspecting articles for features. As shown in each of FIGS. 2A-2D, polarized incident light hv or a ray thereof may be specularly reflected from one or more surfaces of an article 200. The one or more surfaces of the article may respectively correspond to one or more layers of the article including, but not limited to, one or more layers selected from a first layer 202, a second layer 204, and a third layer 206. For example, the article 200 may be a hard disk or a workpiece thereof, wherein the first layer 202 is a lubricant layer overlying the second layer 204, wherein the second layer 204 is a carbon overcoat layer overlying the third layer 206, and wherein the third layer 206 is a layer stack including at least a magnetic recording layer. Depending upon characteristics of each of the one or more layers including composition, dimensions (e.g., thickness), and/or features (e.g., defects), the polarized incident light may be specularly reflected from the one or more surfaces of the article to provide mixedly polarized reflected light including p-polarized reflected light, s-polarized reflected light, and q-polarized reflected light. While not shown in FIGS. 2A-2D, the mixedly polarized reflected light may further include circularly polarized light and elliptically polarized light. A reflected light-selecting means 210 may be used to select a particular polarized reflected light to effect a desired combination of polarized incident light and polarized reflected light for inspecting articles.

FIG. 2A provides a schematic illustrating a combination of p-polarized incident light upon a surface of an article and selected p-polarized reflected light from the surface of the article. As shown, p-polarized incident light may be specularly reflected from one or more surfaces of an article to provide mixedly polarized reflected light including at least p-polarized reflected light, s-polarized reflected light, and q-polarized reflected. A reflected light-selecting means 210 may be used to select p-polarized reflected light to effect a combination of p-polarized incident light and p-polarized reflected light for inspecting articles.

FIG. 2B provides a schematic illustrating a combination of p-polarized incident light upon a surface of an article and selected s-polarized reflected light from the surface of the article. As shown, p-polarized incident light may be specularly reflected from one or more surfaces of an article to provide mixedly polarized reflected light including at least p-polarized reflected light, s-polarized reflected light, and q-polarized reflected. A reflected light-selecting means 210 may be used to select s-polarized reflected light to effect a combination of p-polarized incident light and s-polarized reflected light for inspecting articles.

FIG. 2C provides a schematic illustrating a combination of s-polarized incident light upon a surface of an article and selected s-polarized reflected light from the surface of the article. As shown, s-polarized incident light may be specularly reflected from one or more surfaces of an article to provide mixedly polarized reflected light including at least p-polarized reflected light, s-polarized reflected light, and q-polarized reflected. A reflected light-selecting means 210 may be used to select s-polarized reflected light to effect a combination of s-polarized incident light and s-polarized reflected light for inspecting articles.

FIG. 2D provides a schematic illustrating a combination of s-polarized incident light upon a surface of an article and selected p-polarized reflected light from the surface of the article. As shown, s-polarized incident light may be specularly reflected from one or more surfaces of an article to provide mixedly polarized reflected light including at least p-polarized reflected light, s-polarized reflected light, and q-polarized reflected. A reflected light-selecting means 210 may be used to select p-polarized reflected light to effect a combination of s-polarized incident light and p-polarized reflected light for inspecting articles.

Apparatuses and methods for inspecting articles for features employ various combinations of components for detecting, mapping, and/or distinguishing features of articles.

FIGS. 3A and 3B provide schematics illustrating some of the various combinations of components for detecting, mapping, and/or distinguishing features of articles. As shown in each of FIGS. 3A and 3B, an apparatus 300 may include, but is not limited to, a lighting side of the apparatus including lighting-side components and a detecting side of the apparatus including detecting-side components. The lighting-side components may include, but are not limited to, a light source assembly 310 and a lighting lens assembly 320. Depending upon the light source assembly and the quality of light therefrom, the lighting-side components may further optionally include one or more lighting optical devices 330. The detecting-side components may include, but are not limited to, an image sensor assembly 340, an imaging lens assembly 350, and one or more imaging optical devices 360. The apparatus may further include a processing means 370. While not shown in FIGS. 3A and 3B, the apparatus may further include a stage configured to support an article. The stage may be further optionally configured to rotate the article, if desired, for piecewise inspection.

Turning to the lighting-side of the apparatus, the light source assembly 310 and the lighting lens assembly 320 shown in each of FIGS. 3A and 3B may be optionally positioned at different angles such that an article plane a corresponding to a surface of an article, a light source plane b corresponding to a light source of the light source assembly, and a lens plane c corresponding to a lighting lens of the lighting lens assembly converge at Scheimpflug intersection Q. Because the light source assembly and the lighting lens assembly are positioned at a side of the article for illuminating the surface the article, it may be important to employ a Scheimpflug correction in accordance with the Scheimpflug principle to uniformly illuminate the entire surface of the article or a predetermined portion thereof. Otherwise, time-intensive rotation of the article, translation of the article, or both may be required to uniformly illuminate the entire surface of the article or the predetermined portion thereof over time. A Scheimpflug correction may not be needed for the light source assembly and the lighting lens assembly if the light is sufficiently afocal therefrom.

It should be understood that uniformly or homogeneously illuminating an entire surface of an article or a predetermined portion thereof may include, but is not limited to, subjecting the entire surface of the article or the predetermined portion thereof to the same or about the same quantity of light per unit time, the same or about the same radiant energy per unit time (e.g., radiant power or radiant flux), or the same or about the same radiant power per unit area (e.g., irradiance or radiant flux density).

As further shown in each of FIGS. 3A and 3B, the light source assembly 310 and the lighting lens assembly 320 may be positioned at a particular distance and/or angle for illuminating a surface an article. The distance and/or angle may be optimized for one or more types of features.

The light source assembly 310 and the lighting lens assembly 320 may be positioned for illuminating a surface of an article at an angle of incidence ranging from greater than 0° to less than 90°, wherein an angle of incidence of about 0° represents illuminating the surface of the article from directly above the article, and wherein an angle of incidence of about 90° represents illuminating the surface of the article side-on. In some non-limiting embodiments, for example, the light source assembly and the lighting lens assembly are positioned for illuminating the surface of the article at Brewster's angle for one or more surfaces of the article or one or more types of features thereof. In such embodiments, illuminating the surface of the article at Brewster's angle may allow for maximal difference in p-polarized and s-polarized reflected light for the one or more surfaces of the article or the one or more types of features thereof. In some non-limiting embodiments, for example, the light source assembly and the lighting lens assembly are positioned for illuminating the surface of the article at an angle other than Brewster's angle for one or more surfaces of the article or one or more types of features thereof.

The light source assembly 310 and the lighting lens assembly 320 may be positioned for illuminating a surface of an article at a glancing angle ranging from greater than 0° to less than 90°, wherein a glancing angle of about 0° represents illuminating the surface of the article side-on, and wherein a glancing angle of about 90° represents illuminating the surface of the article from directly above the article. In some non-limiting embodiments, for example, the light source assembly and the lighting lens assembly are positioned for illuminating the surface of the article at a glancing angle greater than 0°, 5°, 10°, 15°, 20°, 25°, 30°, 35°, 40°, 45°, 50°, 55°, 60°, 65°, 70°, 75°, 80°, or 85°. In some non-limiting embodiments, for example, the light source assembly and the lighting lens assembly are positioned for illuminating the surface of the article at a glancing angle less than 90°, 85°, 80°, 75°, 70°, 65°, 60°, 55°, 50°, 45°, 40°, 35°, 30°, 25°, 20°, 15°, 10°, or 5°. Combinations of the foregoing may be used to describe the glancing angle for illuminating the surface of the article. In some non-limiting embodiments, for example, the light source assembly and the lighting lens assembly are positioned for illuminating the surface of the article at a glancing angle greater than 0° and less than 90° (i.e., between 0° and) 90°, including greater than 0° and less than 45° (i.e., between 0° and 45°), and including greater than 45° and less than 90° (i.e., between 45° and 90°). Because the glancing angle and the angle of incidence are complementary angles, it should be understood that the foregoing may be equally expressed in terms of the angle of incidence.

The light source assembly 310 may include a light source operable to provide light for homogeneously illuminating an entire surface of an article or a predetermined portion thereof.

The light source may be configured to provide light including any one or more characteristics. The light source may be configured to provide light including a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic) for homogeneously illuminating an entire surface of an article or a predetermined portion thereof. In terms of frequency, the light source may be configured to provide light including a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic) for homogeneously illuminating an entire surface of an article or a predetermined portion thereof. The light source may be configured to provide light including unpolarized light or polarized light for homogeneously illuminating an entire surface of an article or a predetermined portion thereof, wherein the polarized light includes linearly polarized light (e.g., p-polarized light, s-polarized light, q-polarized light, etc.), circularly polarized light, or elliptically polarized light. The light source may be configured to provide light including a certain degree of spatial and/or temporal coherence ranging from noncoherent light to coherent light (e.g., laser) for homogeneously illuminating an entire surface of an article or a predetermined portion thereof.

One or more lighting optical devices 330 shown in each of FIGS. 3A and 3B may be used in conjunction with the light source assembly 310 to provide light including any one or more of the characteristics described herein to a surface of an article. The one or more lighting optical devices may include, but are not limited to, one or more lighting optical devices selected from filters (e.g., polarizers, neutral density filters), compensators (e.g., retarders such variable retarders or waveplates such as quarter-wave plates and half-wave plates), and photoelastic modulators in any desired combination and/or order. The one or more lighting optical devices may establish a polarization management device or an incident light-selecting means operable to select a particular polarized incident light for illuminating a surface of an article. In some non-limiting embodiments, for example, the polarization management device or the incident light-selecting means is operable to select any one of p-polarized incident light, s-polarized incident light, or q-polarized incident light for illuminating a surface of an article at any given time.

Turning to the detecting-side of the apparatus, the image sensor assembly 340 and the imaging lens assembly 350 shown in each of FIGS. 3A and 3B may be positioned at different angles such that the article plane a, an image sensor plane d corresponding to an image sensor of the image sensor assembly, and a lens plane e corresponding to an imaging lens of the imaging lens assembly converge at Scheimpflug intersection R. Because the imaging sensor assembly and the imaging lens assembly are positioned at a side of the article for detecting specularly reflected light from the surface of the article, it is important to employ a Scheimpflug correction in accordance with the Scheimpflug principle to bring the entire surface of the article into the plane of focus. Otherwise, only a small portion of the entire surface of the article would be in the plane of focus at any given time requiring time-intensive rotation of the article, translation of the article, or both to bring the entire surface of the article into the plane of focus over time.

As further shown in each of FIGS. 3A and 3B, the image sensor assembly 340 and the imaging lens assembly 350 may be positioned at a particular distance and/or angle for detecting specularly reflected light from a surface of an article. The distance and/or angle may be optimized for one or more types of features.

The image sensor assembly 340 and the imaging lens assembly 350 may be positioned for detecting specularly reflected light from a surface of an article at an angle of reflection matching the angle of incidence at which the light source assembly 310 and the lighting lens assembly 320 are positioned for illuminating the surface of the article.

The image sensor assembly 340 and the imaging lens assembly 350 may be positioned for detecting specularly reflected light from a surface of an article at an angle (e.g., the angle $\beta_2$ of FIGS. 1D-1F) matching the glancing angle at which the light source assembly 310 and the lighting lens assembly 320 are positioned for illuminating the surface of the article.

The image sensor assembly 340 may include an image sensor operable to detect specularly reflected light from one or more surfaces of an article and convert the light into electronic signals for processing by the processing means 370.

The image sensor may be configured to detect light including any one or more characteristics. The image sensor may be configured to detect light including a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic) and convert the light into electronic signals for processing by the processing means. In terms of frequency, the image sensor may be configured to detect light including a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic) and convert the light into electronic signals for processing by the processing means. The image sensor may be configured to detect light including unpolarized light or polarized light and convert the light into electronic signals for processing by the processing means, wherein the polarized light includes linearly polarized light (e.g., p-polarized light, s-polarized light, q-polarized light, etc.), circularly polarized light, or elliptically polarized light. The light source may be configured to detect light including a certain degree of spatial and/or temporal coherence ranging from noncoherent light to coherent light (e.g., laser) and convert the light into electronic signals for processing by the processing means.

The image sensor may include a number of light sensor elements or pixels, each of which may include a photodetector and one or more readout devices (e.g., capacitors, transistors, etc.).

The number of pixels may be arranged in n rows and m columns of a two-dimensional array, and the number of pixels n×m or resolution may be expressed in millions of pixels or megapixels ("MP"). For example, the number of pixels may be arranged in 2048 rows and 2048 columns of a two-dimensional array, and the number of pixels 2048×2048 may be expressed as 4.2 MP. For example, the number of pixels may be arranged in 2560 rows and 2160 columns of a two-dimensional array, and the number of pixels 2560×2160 may be expressed as 5.5 MP. It should be understood that the image sensor is not limited to the foregoing numbers of pixels as the image sensor may include more or fewer pixels than either of the foregoing numbers of pixels.

Each pixel may be a rectangle or square in shape, and each pixel may be micrometer sized (i.e., admits of μm units as measured) in at least one of a length or a width. For example, each pixel may be a rectangle in shape, and each pixel may be about 6.5 μm in at least one of a length or a width. For example, each pixel may be a square in shape, and each pixel may be about 6.5 μm in length and width. It should be understood that the image sensor is not limited to pixels of the foregoing shapes as the image sensor may include pixels of any of a number of shapes different than the foregoing shapes. It should be understood that the image sensor is not limited to pixels of the foregoing size as the image sensor may include pixels of any of a number of sizes (e.g., from about 3 μm to about 15 μm) different than the foregoing size.

Each pixel may correspond to a particular, fixed area of a surface of an article, and each pixel may respectively correspond to a particular, fixed area of a features map. In other words, there may be a one-to-one-to-one correspondence between a particular, fixed area of a surface of an article, a pixel of the image sensor, and a particular, fixed area of a features map. Such correspondence facilitates identification of a particular feature's coordinates about an article for further analysis, optionally with additional analytical instrumentation. Such correspondence across a number of articles facilitates identification of article-over-article defects and correction of manufacturing trends.

The image sensor may include, but is not limited to, a charge-coupled device ("CCD"), an intensified charge-coupled device ("ICCD"), an electron-multiplying charge-coupled device ("EMCCD"), a complementary metal-oxide semiconductor ("CMOS"), or a scientific complementary metal-oxide semiconductor ("sCMOS").

The image sensor assembly 340 may include, but is not limited to, a CCD camera, an ICCD camera, an EMCCD camera, a CMOS camera, or an sCMOS camera.

The imaging lens assembly 350 may include a lens operable to collect specularly reflected light from one or more surfaces of an article and provide the light to the image sensor assembly 340.

The lens may include, but is not limited to, an objective lens. An objective lens may include a telecentric lens, which reduces errors with respect to feature position, and which reduces optical aberration. For example, the lens may include, but is not limited to, an object-space telecentric lens (i.e., entrance pupil at infinity), an image-space telecentric lens (i.e., exit pupil at infinity), or a double telecentric lens (i.e., entrance and exit pupils at infinity). It should be understood that the lens is not limited to the foregoing lenses as the lens may include any of a number of lenses different than the foregoing lenses.

One or more imaging optical devices 360 shown in each of FIGS. 3A and 3B may be used in conjunction with the imaging lens assembly 350 to provide light including any one or more of the characteristics described herein to the image sensor assembly 340. The one or more imaging optical devices may include, but are not limited to, one or more imaging optical devices selected from filters (e.g., polarizers, neutral density filters), compensators (e.g., retarders such as variable retarders or waveplates such as quarter-wave plates and half-wave plates), and photoelastic modulators in any desired combination and/or order. The one or more imaging optical devices may establish a polarization management device or a reflected light-selecting means operable to select a particular polarized reflected light for the image sensor assembly. In some non-limiting embodiments, for example, the polarization management device or the reflected light-selecting means is operable to select any one of p-polarized reflected light, s-polarized reflected light, or q-polarized reflected light for the image sensor assembly.

Turning to the processing means of the apparatus, the processing means 370 shown in each of FIGS. 3A and 3B may include one or more computers or equivalent devices including primary and/or secondary memory and one or more processing elements operable to carry out arithmetic and logical operations. The one or more computers or equivalent devices may include, but are not limited to, one or more computers or equivalent devices selected from servers, workstations, desktop computers, nettops, laptops, netbooks, and mobile devices including tablets and smartphones. The one or more computers or equivalent devices may contain graphics processing units ("GPU"s), application-specific integrated circuits ("ASIC"s), field-programmable gate arrays ("FPGA"s), etc.

The processing means 370 may include or have access to instructions for conveying articles to the apparatus; positioning articles for inspection, optionally including gradationally or continuously rotating articles for inspection; inserting optical devices into the incident light path and/or the reflected light path; positioning optical devices in the incident light path and/or the reflected light path; tuning optical devices (e.g., piezoelectric-based polarization management devices); removing optical devices from the incident light path and/or the reflected light path; positioning the light source assembly and the lighting lens assembly in accordance with the Scheimpflug principle; positioning the light source assembly and the lighting lens assembly in accordance with an optimum distance and/or angle for one or more types of features; switching the light source on and off or otherwise between modes for providing light and not providing light; positioning the image sensor assembly and the imaging lens assembly in accordance with the Scheimpflug principle; positioning the image sensor assembly and the imaging lens assembly in accordance with an optimum distance and/or angle for one or more types of features; switching the image sensor on and off or otherwise between modes for detecting light and not detecting light; and/or synchronizing the light source with the image sensor.

The processing means 370 may include or have access to instructions for processing electronic signals from the image sensor assembly 340 for detecting, mapping, and/or distinguishing features of articles. The electronic signals from the image sensor may correspond to image sensor-detected light resulting from different selections or combinations of polarized incident light and polarized reflected light. For example, as shown in FIGS. 2A-2D, some combinations of polarized incident light and polarized reflected light include, but are not limited to, p-polarized incident light and p-polarized reflected light; p-polarized incident light and s-polarized reflected light; s-polarized incident light and p-polarized reflected light; and s-polarized incident light and s-polarized reflected light. It should be understood that combinations of polarized incident light and polarized reflected light are not limited to the foregoing combinations as any of a number of combinations different than the foregoing may be used. For example, q-polarized incident light and/or q-polarized reflected light may be used in combinations.

The processing means 370 may generate features maps corresponding to the electronic signals from the image sensor assembly 340, each of which features maps may provide differentiating or distinguishing information for one or more types of features. The distinguishing information is in accordance with different combinations of polarized incident light and polarized reflected light, each of which combinations may interact differently with one or more types of features. FIG. 4 provides an image of such a features map 400 including a defect 410.

The processing means 370 may generate any of a number of features maps corresponding to the electronic signals from the image sensor assembly 340. For example, the processing means may generate a features map for a combination of p-polarized incident light and p-polarized reflected light; p-polarized incident light and s-polarized reflected light; s-polarized incident light and p-polarized reflected light; and/or s-polarized incident light and s-polarized reflected light. Because any of a number of combinations of polarized incident light and polarized reflected light different than the foregoing may be used including q-polarized incident light and/or q-polarized reflected light, the processing means may generate features maps 400A, 400B, 400C, . . . , 400n, wherein n indicates the $n^{th}$ features map for the $n^{th}$ desired combination of polarized incident light and polarized reflected light.

The processing means 370 may generate one or more polarization contrast maps or composite features maps from any two or more features maps or the information sufficient to produce them. A composite features map may enhance one or more types of features between any two or more features maps. A composite features map may consolidate one or more types of features onto the composite features map from any two or more features maps including different types of features between them. The one-to-one-to-one correspondence between a particular, fixed area of a surface of an article, a pixel of the image sensor, and a particular, fixed area of a features map facilitates generating the one or more composite features maps.

The processing means 370 may increase pixel resolution for one or more features map with pixel interpolation. Pixel interpolation may increase pixel resolution about 10× or more without an increase in pixels in the image sensor.

The apparatus 300 shown in each of FIGS. 3A and 3B may be configured to inspect articles for features at a rate commensurate with or greater than the rate at which the articles or workpieces thereof are produced. In some non-limiting embodiments, for example, the apparatus is configured to inspect articles at a rate of at least 1, 2, 3, 4, 5, 6, 7, 8, 9, 10, 12, 14, 16, 18, or 20 article(s) per second, or greater. Inspecting articles for features at a rate commensurate with or greater than the rate at which the articles or workpieces thereof are produced is a function of many features of the apparatus including, but not limited to, maintaining the linear and the angular position of articles while inspecting them.

In view of the foregoing, FIG. 3A provides a schematic illustrating some embodiments of an apparatus for detecting, mapping, and/or distinguishing features of articles. As shown in FIG. 3A, an apparatus 300 may include, but is not limited to, a lighting side of the apparatus including lighting-side components and a detecting side of the apparatus including detecting-side components.

The lighting-side components of the apparatus 300 of FIG. 3A may include, but are not limited to, a light source assembly 310 and a lighting lens assembly 320, wherein the light source assembly and the lighting lens assembly are optionally adjusted in accordance with the Scheimpflug principle.

The light source assembly 310 may include, but is not limited to, a high-speed flash lamp (e.g., 5 mW-500 W Xe flash lamp) for minimizing vibration while detecting specularly reflected light from a surface of an article.

The lighting-side components of the apparatus 300 of FIG. 3A may optionally include one or more lighting optical devices 330 including, but not limited to, one or more lighting optical devices selected from a neutral density filter 332, a polarizer 334 (e.g., linear polarization filter), and a compensator 336 (e.g., variable retarder or quarter-wave plate).

The detecting-side components of the apparatus 300 of FIG. 3A may include, but are not limited to, an image sensor assembly 340, an imaging lens assembly 350, and one or more imaging optical devices 360, wherein the image sensor assembly and the imaging lens assembly are adjusted in accordance with the Scheimpflug principle.

The image sensor assembly 340 may include, but is not limited to, an sCMOS image sensor.

The imaging lens assembly 350 may include, but is not limited to, a telecentric lens for reducing feature-position errors and optical aberrations.

The imaging optical devices 360 may include, but are not limited to, one or more imaging optical devices selected from a polarizer 364 (e.g., linear polarization filter), and a compensator 366 (e.g., variable retarder or quarter-wave plate).

Features of the processing means 370 of the apparatus 300 of FIG. 3A are described herein.

Also in view of the foregoing, FIG. 3B provides a schematic illustrating some embodiments of an apparatus for detecting, mapping, and/or distinguishing features of articles. As shown in FIG. 3B, an apparatus 300 may include, but is not limited to, a lighting side of the apparatus including lighting-side components and a detecting side of the apparatus including detecting-side components.

The lighting-side components of the apparatus 300 of FIG. 3B may include, but are not limited to, a light source assembly 310 and a lighting lens assembly 320, wherein the light source assembly and the lighting lens assembly are optionally adjusted in accordance with the Scheimpflug principle.

The light source assembly 310 may include, but is not limited to, a first light source 312 at an angle to a second light source 314 with a beam-splitting-and-light-trapping assembly 316 therebetween, wherein the angle is sufficient for optimal beam splitting with the beam-splitting assembly. The first light source may provide incident light of a first polarization (e.g., p-polarized incident light) to the beam-splitting-and-light-trapping assembly, wherein a beam splitter transmits a portion of the light for illuminating a surface of an article and reflects a portion of the light to a light trap. The second light source may provide incident light of a second polarization (e.g., s-polarized incident light) to the beam-splitting-and-light-trapping assembly, wherein the beam splitter reflects a portion of the light for illuminating a surface of an article and transmits a portion of the light to the light trap.

The lighting-side components of the apparatus 300 of FIG. 3B may optionally include one or more lighting optical devices 330 including, but not limited to, one or more lighting optical devices selected from a neutral density filter 332, a polarizer 334 (e.g., linear polarization filter), and a compensator 336 (e.g., variable retarder or quarter-wave plate).

The detecting-side components of the apparatus 300 of FIG. 3B may include, but are not limited to, an image sensor assembly 340, an imaging lens assembly 350, and one or more imaging optical devices 360, wherein the image sensor assembly and the imaging lens assembly are adjusted in accordance with the Scheimpflug principle.

The image sensor assembly 340 may include, but is not limited to, a first image sensor 342 at an angle to a second image sensor 344 with a beam-splitting assembly 346 therebetween, wherein the angle is sufficient for optimal beam splitting with the beam-splitting assembly, optionally from about 57° to about 60°. The beam-splitting assembly may be configured to split specularly reflected light from a surface of an article into reflected light of a first polarization (e.g., p-polarized incident light) and reflected light of a second polarization (e.g., s-polarized incident light). The beam-splitting assembly may be configured to provide the light of the first polarization to the first image sensor and provide the light of the second polarization to the second image sensor, each of which image sensor may be an sCMOS image sensor.

The imaging lens assembly 350 may include, but is not limited to, a telecentric lens for reducing feature-position errors and optical aberrations.

The imaging optical devices 360 may include, but are not limited to, one or more imaging optical devices selected from a polarizer 364 (e.g., linear polarization filter), and a compensator 366 (e.g., variable retarder or quarter-wave plate).

Features of the processing means 370 of the apparatus 300 of FIG. 3B are described herein.

As such, provided herein is an apparatus, comprising an imaging lens assembly configured to collect reflected light from a surface of an article; an image sensor configured to receive reflected light from the imaging lens assembly, wherein the imaging lens assembly and the image sensor are each arranged at different angles for focusing on substantially an entire surface of an article; and a processing means configured to process signals from the image sensor corresponding to polarized reflected light and subsequently generate one or more features maps. In some embodiments, the imaging lens assembly comprises a telecentric lens, and the image sensor comprises at least about 5.5 megapixels. In some embodiments, the apparatus further comprises a reflected light-selecting means for selecting a polarized reflected light for the image sensor, wherein the polarized reflected light is selected from p-polarized reflected light and s-polarized reflected light. In some embodiments, the apparatus is configured to provide one of p-polarized reflected light or s-polarized reflected light to the image sensor at a time. In some embodiments, the image sensor comprises a first image sensor at an angle to a second image sensor, wherein the apparatus is configured to provide one of p-polarized reflected light or s-polarized reflected light to the first image sensor, and wherein the apparatus is configured to provide the other one of p-polarized reflected light or s-polarized reflected light to the second image sensor at the same time or a different time. In some embodiments, the apparatus further comprises a lighting lens assembly configured to receive light from a light source, wherein the light source and the lighting lens assembly are each arranged at different angles for uniformly illuminating substantially an entire surface of an article. In some embodiments, the imaging lens assembly and the image sensor are each arranged at different angles in accordance with the Scheimpflug principle, and the light source and the lighting lens assembly are each arranged at different angles in accordance with the Scheimpflug principle. In some embodiments, the apparatus further comprises an incident light-selecting means for selecting a polarized incident light for a surface of an article, wherein the polarized incident light is selected from p-polarized incident light, s-polarized incident light, and q-polarized incident light. In some embodiments, the light source comprises a first light source at an angle to a second light source, wherein the first light source is configured to provide one of p-polarized incident light, s-polarized incident light, or q-polarized incident light, and wherein the second light source is configured to provide any other one of p-polarized incident light, s-polarized incident light, or q-polarized incident light at the same time or a different time. In some embodiments, the apparatus is configured to maintain a linear and an angular position of an article while imaging a surface of the article. In some embodiments, the one or more features maps are generated from different combinations of polarized incident light and polarized reflected light, wherein the polarized incident light is selected from p-polarized incident light, s-polarized incident light, and q-polarized incident light, and wherein the polarized reflected light is selected from p-polarized reflected light and s-polarized reflected light. In some embodiments, the features of the one or more features maps are selected from thickness of one or more layers of a hard disk or a workpiece thereof; homogeneity of one or more layers of a hard disk or a workpiece thereof; and stains in one or more layers of a hard disk or a workpiece thereof.

Also provided herein is an apparatus, comprising a lighting lens assembly configured to receive light from a light source, wherein the light source and the lighting lens assembly are each arranged at different angles for illuminating substantially an entire surface of an article; an imaging lens assembly configured to collect reflected light from a surface of an article; an image sensor configured to receive reflected light from the imaging lens assembly, wherein the imaging lens assembly and the image sensor are each arranged at different angles for focusing on substantially an entire surface of an article; and a processing means configured to process signals from the image sensor corresponding to polarized reflected light and subsequently generate one or more features maps. In some embodiments, the one or more features maps are generated from different combinations of polarized incident light and polarized reflected light, wherein the polarized incident light is selected from p-polarized incident light, s-polarized incident light, and q-polarized incident light, and wherein the polarized reflected light is selected from p-polarized reflected light and s-polarized reflected light. In some embodiments, the apparatus further comprises an incident light-selecting means for selecting a polarized incident light for a surface of an article, wherein the polarized incident light is selected from p-polarized incident light, s-polarized incident light, and q-polarized incident light. In some embodiments, the apparatus further comprises a reflected light-selecting means for selecting a polarized reflected light for the image sensor, wherein the polarized reflected light is selected from p-polarized reflected light and s-polarized reflected light, and wherein the apparatus is configured to provide one of p-polarized reflected light or s-polarized reflected light to the image sensor at a time.

Also provided herein is an apparatus, comprising a lighting lens assembly configured to receive light from a first light source and second light source at an angle to the first light source, wherein the light sources and the lighting lens assembly are each arranged at different angles for illuminating substantially an entire surface of an article; an imaging lens assembly configured to collect reflected light from a surface of an article; a first image sensor at an angle to a second image sensor configured to receive reflected light from the imaging lens assembly, wherein the imaging lens assembly and the image sensors are each arranged at different angles for focusing on substantially an entire surface of an article; and a processing means configured to process signals from the image sensors corresponding to polarized reflected light and subsequently generate one or more features maps. In some embodiments, the one or more features maps are generated from different combinations of polarized incident light and polarized reflected light, wherein the polarized incident light is selected p-polarized incident light, s-polarized incident light, and q-polarized incident light, and wherein the polarized reflected light is selected from p-polarized reflected light and s-polarized reflected light. In some embodiments, the first light source is configured to provide one of p-polarized incident light, s-polarized incident light, or q-polarized incident light, and the second light source is configured to provide any other one of p-polarized incident light, s-polarized incident light, or q-polarized incident light at the same time or a different time. In some embodiments, the apparatus further comprises a reflected light-selecting means for selecting a polarized reflected light for the image sensor, wherein the polarized reflected light is selected from p-polarized reflected light and s-polarized reflected light, wherein the apparatus is configured to provide one of p-polarized reflected light or s-polarized reflected light to the first image sensor, and wherein the apparatus is configured to provide the other one of p-polarized reflected light or s-polarized reflected light to the second image sensor at the same time or a different time.

While some particular embodiments have been described and/or illustrated herein, and while these particular embodiments have been described and/or illustrated in considerable detail, it is not the intention for these particular embodiments to limit the scope of the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts provided herein. The implementations provided herein and other implementations are within the scope of the following claims.

What is claimed is:

1. An apparatus, comprising:
   an imaging lens assembly, including a lens configured to collect a polarized reflected light from an entire surface of an article;
   an image sensor configured to receive the polarized reflected light from the lens of the imaging lens assembly, wherein the imaging lens assembly and the image sensor are each arranged at different angles for focusing on substantially the entire surface of the article; and
   a processing means configured to process signals from the image sensor corresponding to the polarized reflected light and subsequently generate one or more feature maps.

2. The apparatus of claim 1,
   wherein the lens of the imaging lens assembly comprises a telecentric lens, and
   wherein the image sensor comprises at least about 5.5 megapixels.

3. The apparatus of claim 1, wherein the apparatus is configured to provide one of the p-polarized reflected light or the s-polarized reflected light to the image sensor at a time.

4. The apparatus of claim 1, wherein the image sensor comprises a first image sensor at an angle to a second image sensor, wherein the apparatus is configured to provide one of the p-polarized reflected light or the s-polarized reflected light to the first image sensor, and wherein the apparatus is configured to provide the other one of the p-polarized reflected light or the s-polarized reflected light to the second image sensor at the same time or a different time.

5. The apparatus of claim 1, further comprising:
   a lighting lens assembly configured to receive light from a light source,
   wherein the light source and the lighting lens assembly are each arranged at different angles for uniformly illuminating substantially the entire surface of the article.

6. The apparatus of claim 5,
   wherein the imaging lens assembly and the image sensor are each arranged at different angles in accordance with the Scheimpflug principle, and
   wherein the light source and the lighting lens assembly are each arranged at different angles in accordance with the Scheimpflug principle.

7. The apparatus of claim 5,
   wherein the light source comprises a first light source at an angle to a second light source,
   wherein the first light source is configured to provide one of the p-polarized incident light, the s-polarized incident light, or the q-polarized incident light, and
   wherein the second light source is configured to provide any other one of the p-polarized incident light, the s-polarized incident light, or the q-polarized incident light at the same time or a different time.

8. The apparatus of claim 1,
   wherein the apparatus is configured to maintain a linear and an angular position of an article while imaging the surface of the article.

9. The apparatus of claim 1,
   wherein the one or more features maps are generated from different combinations of the polarized incident light and the polarized reflected light,
   wherein the polarized incident light is selected from the p-polarized incident light, the s-polarized incident light, and the q-polarized incident light, and
   wherein the polarized reflected light is selected from the p-polarized reflected light and the s-polarized reflected light.

10. The apparatus of claim 1,
    wherein the features of the one or more features maps are selected from a thickness of one or more layers of a hard disk or a workpiece thereof; a homogeneity of one or more layers of the hard disk or the workpiece thereof; and one or more stains in one or more layers of the hard disk or the workpiece thereof.

11. An apparatus, comprising:
a lighting lens assembly configured to receive a light from a light source,
   wherein the light source and the lighting lens assembly are each arranged at different angles for illuminating substantially an entire surface of an article;
an imaging lens assembly, including a lens configured to collect a reflected light from the entire surface of the article;
an image sensor configured to receive the reflected light from the lens of the imaging lens assembly,
   wherein the imaging lens assembly and the image sensor are each arranged at different angles for focusing on substantially the entire surface of the article; and
a processing means configured to process signals from the image sensor corresponding to a polarized reflected light and subsequently generate one or more features maps.

12. The apparatus of claim 11,
wherein the one or more features maps are generated from different combinations of a polarized incident light and the polarized reflected light,
wherein the polarized incident light is selected from a p-polarized incident light, an s-polarized incident light, and a q-polarized incident light, and
wherein the polarized reflected light is selected from a p-polarized reflected light and an s-polarized reflected light.

13. An apparatus, comprising:
a lighting lens assembly configured to receive a light from a first light source and second light source at an angle to the first light source,
   wherein the light sources and the lighting lens assembly are each arranged at different angles for illuminating substantially an entire surface of an article;
an imaging lens assembly, including a lens, configured to collect a reflected light from the entire surface of the article;
a first image sensor at an angle to a second image sensor configured to receive the reflected light from the lens of the imaging lens assembly,
   wherein the imaging lens assembly and the image sensors are each arranged at different angles for focusing on substantially the entire surface of the article; and
a processing means configured to process signals from the image sensors corresponding to a polarized reflected light and subsequently generate one or more features maps.

14. The apparatus of claim 13,
wherein the one or more features maps are generated from different combinations of a polarized incident light and the polarized reflected light,
wherein the polarized incident light is selected from a p-polarized incident light, an s-polarized incident light, and a q-polarized incident light, and
wherein the polarized reflected light is selected from a p-polarized reflected light and an s-polarized reflected light.

15. The apparatus of claim 14,
wherein the first light source is configured to provide one of the p-polarized incident light, the s-polarized incident light, or the q-polarized incident light, and
wherein the second light source is configured to provide any other one of the p-polarized incident light, the s-polarized incident light, or the q-polarized incident light at the same time or a different time.

* * * * *